(12) United States Patent
Fukunaga

(10) Patent No.: US 9,741,194 B2
(45) Date of Patent: Aug. 22, 2017

(54) BANKNOTE DISCRIMINATION APPARATUS

(71) Applicant: OLYMPUS CORPORATION, Tokyo (JP)

(72) Inventor: Yasuhiro Fukunaga, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 62 days.

(21) Appl. No.: 14/963,959

(22) Filed: Dec. 9, 2015

(65) Prior Publication Data

US 2016/0098879 A1    Apr. 7, 2016

Related U.S. Application Data

(63) Continuation of application No. PCT/JP2014/071989, filed on Aug. 22, 2014.

(30) Foreign Application Priority Data

Aug. 30, 2013 (JP) .................................. 2013-179994

(51) Int. Cl.
*G01N 21/64* (2006.01)
*G07D 7/12* (2016.01)

(52) U.S. Cl.
CPC ............. *G07D 7/122* (2013.01); *G01N 21/64* (2013.01); *G01N 21/643* (2013.01); *G01N 21/645* (2013.01); *G01N 2021/6471* (2013.01)

(58) Field of Classification Search
CPC .... G07D 7/122; G01N 21/645; G01N 21/643; G01N 21/64; G01N 2021/6471
USPC ........................................... 250/458.1, 459.1
See application file for complete search history.

(56) References Cited

FOREIGN PATENT DOCUMENTS

| EP | 2 549 445 A1 | 1/2013 |
|---|---|---|
| JP | 2002-109598 A | 4/2002 |
| JP | 2012-58925 A | 3/2012 |
| WO | 2011/114455 A1 | 9/2011 |

OTHER PUBLICATIONS

Translation Takahiro et al., JP2002109598, Published Apr. 12, 2002.*
International Search Report dated Oct. 28, 2014, issued in counterpart Application No. PCT/JP2014/071989 (1 page).

* cited by examiner

*Primary Examiner* — David Porta
*Assistant Examiner* — Gisselle Gutierrez
(74) *Attorney, Agent, or Firm* — Westerman, Hattori, Daniels & Adrian, LLP

(57) ABSTRACT

A banknote discrimination apparatus includes a plurality of photoelectric conversion elements in which an incident light including fluorescence emitted from a banknote irradiated with excitation light enters; a plurality of organic film filters that are arranged so as to overlap each of the plurality of photoelectric conversion elements, and have mutually different transmission bands; a circuit including a plurality of pixel circuits which are each connected to one corresponding element among the plurality of photoelectric conversion elements and output a pixel signal converted by each photoelectric conversion element in accordance with an intensity of the incident light that transmits through the organic film filter and enters to the photoelectric conversion element; a spectral processor; and a discriminator. At least one of the plurality of organic film filters is a filter obtained by overlapping two or more filter layers on each other.

13 Claims, 16 Drawing Sheets

BANKNOTE DISCRIMINATION APPARATUS

This application claims is a continuation application of International Patent Application No. PCT/JP2014/071989, filed on Aug. 22, 2014, whose priority is claimed on Japanese Patent Application No 2013-179994, filed on Aug. 30, 2013, the contents of both of the International Patent Application and the Japanese Patent Application are incorporated herein by reference in their entirety.

BACKGROUND OF THE INVENTION

Field of the Invention

The present invention relates to a banknote discrimination apparatus.

Description of Related Art

Banknote handling apparatuses, such as automated teller machines (ATMs), in which a plurality of sensors, light sources, and the like are arranged in order to discriminate between whether or not a banknote is genuine and the banknote handling apparatuses perform a complex discrimination processing. As one of the representative methods to perform processing to discriminate between whether or not a banknote is genuine, there is a method that discriminates whether or not the banknote is genuine by detecting the spectrum of the fluorescence of a genuine note when a fluorescent material is included in the banknote.

A method described in Japanese Unexamined Patent Application, First Publication No. 2002-109598 will be described. FIG. 24 is a configuration view of a banknote discrimination apparatus that is known in the related art. A banknote 74 sent by a banknote conveying device 75 controlled by a controller/discriminator 76 is irradiated with the light of a light source 71 that is an ultraviolet LED, and a fluorescent substance printed on the banknote 74 is detected by an optical filter fluorescent sensor 73. A detected signal is converted into a voltage by a circuit 72, and is read as a signal pattern corresponding to each pixel of the optical filter fluorescent sensor 73. Whether or not the banknote 74 is genuine is discriminated by comparing the read signal with a signal pattern of a genuine note based on the spectrum of the fluorescent substance printed at a determined position on the banknote recorded in advance in the controller/discriminator 76.

SUMMARY OF THE INVENTION

A banknote discrimination apparatus related to a first aspect of the present invention includes a plurality of photoelectric conversion elements in which an incident light including fluorescence emitted from a banknote irradiated with excitation light enters, a plurality of organic film filters that are arranged so as to overlap each of the plurality of photoelectric conversion elements, and have mutually different transmission bands, a circuit including a plurality of pixel circuits which are respectively connected to one corresponding element among the plurality of photoelectric conversion elements and output a pixel signal converted by each photoelectric conversion element in accordance with an intensity of the incident light that transmits through the organic film filter and enters to the photoelectric conversion element, a spectral processor which outputs incident light intensities of light that has narrower wavelength bands than a wavelength bands of lights that transmit through the organic film filters based on the plurality of pixel signals output by the plurality of pixel circuits, and a discriminator which compares an output pattern output from the spectral processor with a prerecorded signal pattern of a genuine note in order to discriminate between whether or not a banknote is genuine At least one of the plurality of organic film filters is as filter obtained by stacking two more filter layers.

According to a second aspect of the present invention based on the above first aspect, the transmission wavelength band of each of the plurality of organic film filters may include at least a partial band within 380 nm to 1100 nm, and each of the plurality of organic film filters may be any one type of a bandpass filter type, a high-pass filter type, a low-pass filter type, and a band elimination type.

According to a third aspect of the present invention based on the above first aspect or the above second aspect, colors of several filters among the plurality of organic film filters may be the same, and thicknesses of the several filters may be different from each other.

According to a fourth aspect of the present invention based on any one of the above first aspect to the above third aspect, colors of several filters among the plurality of organic film filters may be the same, and concentrations of coloring materials for the several filters may be different from each other.

According to a fifth aspect of the present invention based on any one of the above first aspect to the above fourth aspect, a pixel on which the organic film filter is not arranged may be included.

According to a sixth aspect of the present invention based on any one of the above first aspect to the above fifth aspect the spectral processor may perform the four arithmetic operations on the plurality of pixel signals output by the plurality of pixel circuits, thereby outputting the light intensity of a light of spectral sensitivity characteristics with a band narrower than spectral sensitivity characteristics of the light that transmits through the organic film filter.

According to a seventh aspect of the present invention based on any one of the above first aspect to the above sixth aspect, each of the plurality of pixel circuits may adjust output gains of the pixel circuits according to an output of the spectral processor.

According to an eighth aspect of the present invention based on any one of the above first aspect to the above seventh aspect, the transmission band of the wavelengths of a light detected by the photoelectric conversion element on which each organic film filter is arranged may include at least one of a partial transmission hand of which the full width at half maximum is 45 nm or more and 350 nm or less and the wavelength hand is 380 nm or more and 1100 nm or less, and a partial transmission band of which the full width at half maximum is 150 nm or more and 210 nm or less and the wavelength band is 550 nm or more and 1100 nm or less.

According to a ninth aspect of the present invention based on any one of the above first aspect to the above eighth aspect, each of the plurality of organic film filters may be formed using any one of a filter that transmits red light, a filter that transmits green light, a filter that transmits blue light, a filter that transmits cyan light, a filter that transmits yellow light, a filter that transmits magenta light, and a filter that transmits violet light.

According to as tenth aspect of the present invention based on any one of the above first aspect to the above ninth aspect, the photoelectric conversion element or which each organic film filter is arranged may have a near-infrared light component cutoff filter on a light-receiving surface.

According to an eleventh aspect of the present invention based on any one aspect of the above first aspect to the above tenth aspect, the plurality of organic film filters may be formed on a glass substrate separately from the photoelectric conversion elements.

According to a twelfth aspect of the present invention based on any one aspect of the above first aspect to the above eleventh aspect, the plurality of organic film filters may be arranged on the glass substrate so that a surface of the glass substrate on which the plurality of organic film filters is formed faces light-receiving surfaces of the plurality of photoelectric conversion elements.

According to a thirteenth aspect of the present invention based on any one aspect of the above first aspect to the above twelfth aspect, the plurality of organic film filters may include filters that transmit light of a same color.

DETAILED DESCRIPTION OF THE PREFERRED EMBODIMENTS

Figure 1:
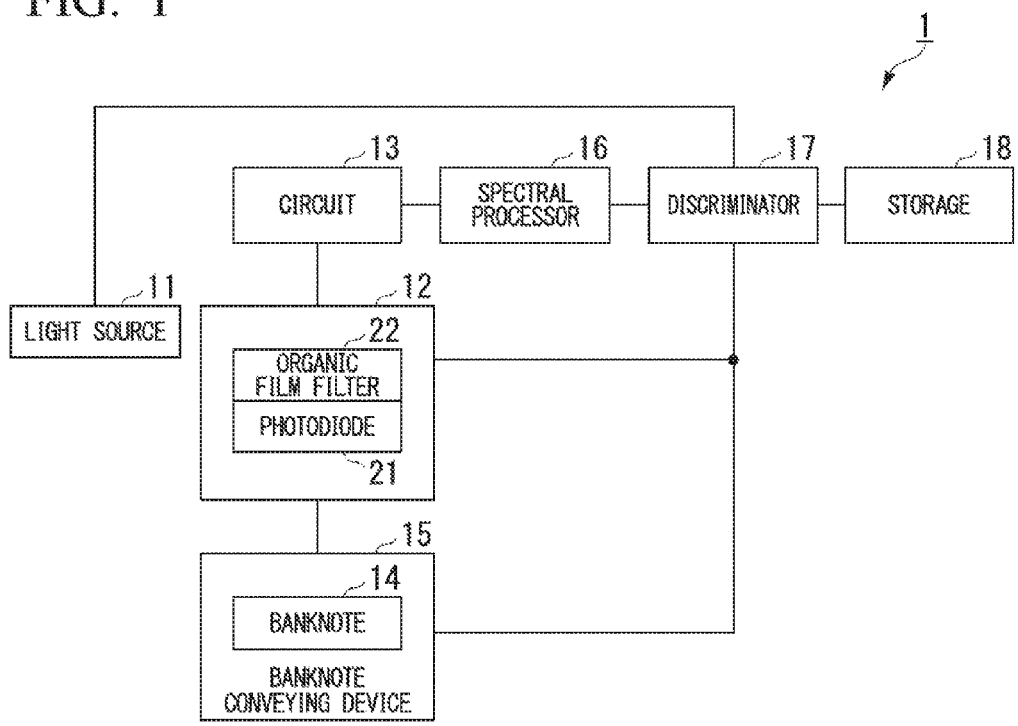
FIG. 1 is a block diagram showing the configuration of a banknote discrimination apparatus in an embodiment of the present invention.

Hereinafter, an embodiment of the present invention will be described with reference to the drawings. FIG. 1 is a block diagram showing the configuration of a banknote discrimination apparatus in the present embodiment. In the shown example, the banknote discrimination apparatus 1 includes a light source 11, an organic multilayer filter fluorescent sensor 12, a circuit 13, a banknote conveying device 15, a spectral processor 16, a discriminator 17, and a storage 18. Additionally, a banknote 14 is placed on the banknote conveying device 15. A fluorescent substance for specifying that the banknote 14 is a genuine note is printed on the banknote 14.

The light source 11 includes, for example, an ultraviolet LED or the like, and radiates excitation light for making the fluorescent substance printed on the banknote 14 emit light. The organic multilayer filter fluorescent sensor 12 photoelectrically converts light that has entered, and outputs pixel signals according to the intensity of the entered light. The details of the organic multilayer filter fluorescent sensor 12 will be described below. The circuit 13 includes a plurality of pixel circuits (not illustrated), each of which amplifies (integrates, allows gain in) and outputs the pixel signals output by the organic multilayer filter fluorescent sensor 12. The pixel circuit may be any common one such as a CMOS image sensor circuit or the like. The banknote conveying device 15 conveys the banknote 14 at a fixed time interval on the basis of the control of the discriminator 17.

The spectral processor 16 performs the four arithmetic operations on the pixel signals output by each of the pixel circuits in the circuit 13, thereby performing spectrum processing. The spectrum processing will be described below. The discriminator 17 controls the respective configuration included in the banknote discrimination apparatus 1. Additionally the discriminator 17 compares the output pattern of a fluorescent material of a genuine note stored in advance by the storage 18 with the pixel signals output by the organic multilayer filter fluorescent sensor 12 and the result obtained by the spectral processor 16 performing the spectrum processing. The discriminator 17 determines whether or not the banknote 14 is a genuine note. In addition, a method for determining whether or not the banknote 14 is a genuine note is performed using the same method as a method known in the related art.

Figure 2:
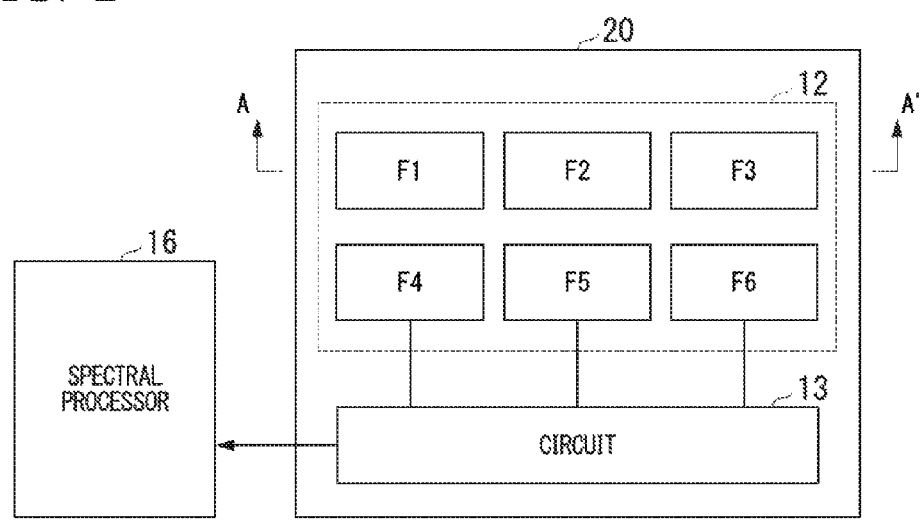
FIG. 2 is a schematic view showing the arrangement of pixels included in an organic multilayer filter fluorescent sensor in the present embodiment.

Next, the configuration of the organic multilayer filter fluorescent sensor 12 will be described. FIG. 2 is a schematic view showing the arrangement of pixels included in the organic multilayer filter fluorescent sensor 12 in the present embodiment. As shown in FIG. 2, the organic multilayer filter fluorescent sensor 12 includes six pixels F of pixels F1 to F6 on a substrate 20. The pixels F include a photodiode (photoelectric conversion element) and an organic film filter. The pixels F1, F3, F5, and F6 include a one-layer organic film filter on a light-receiving surface side of a photodiode. The pixels F2 and F4 include a two-layer organic film filter on a light-receiving surface side of a photodiode. In addition, the substrate 20 is, for example, a silicon substrate, and the photodiodes have a sensitivity of 380 nm to 1100 nm.

Additionally, the number of pixels F included in the organic multilayer filter fluorescent sensor 12 is not limited to six, and may be any number.

Additionally, as shown in FIG. 2, the circuit 13 is formed on the substrate 20. As shown in FIG. 2, the circuit 13 may be formed on the substrate 20 included in the organic multilayer filter fluorescent sensor 12, or may be configured outside of the organic multilayer filter fluorescent sensor 12.

Figure 3:
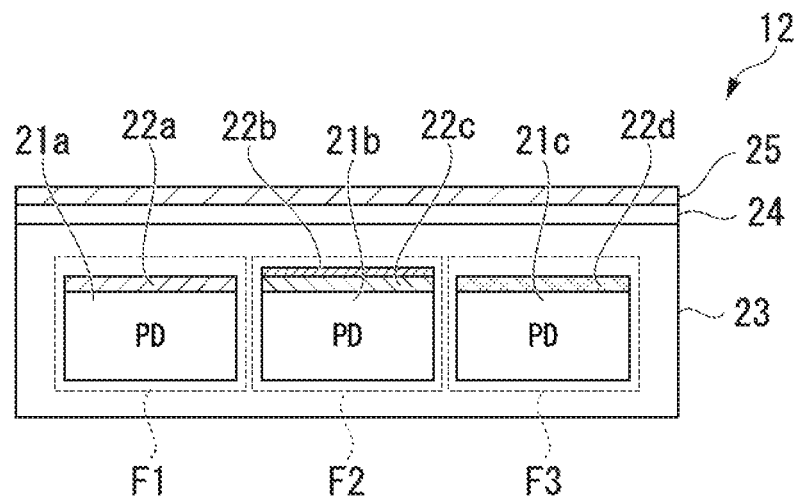
FIG. 3 is a sectional view showing a section of the organic multilayer filter fluorescent sensor in the present embodiment.

FIG. 3 is a sectional view showing a section of the organic multilayer filter fluorescent sensor 12 in the present embodiment. In the shown example, a section taken along A-A' shown in FIG. 2 is shown, and the pixels F1 to F3 are formed on the substrate 20. The pixel F1 includes a photodiode 21a and an organic film filter 22a. The organic film filter 22a is formed on the light-receiving surface side of the photodiode 21a. Additionally the pixel F2 includes a photodiode 21b and organic film filters 22b and 22c. The organic film filters 22b and 22c are formed on the light-receiving surface side of the photodiode 21b. Additionally, the pixel F3 includes a photodiode 21c and an organic film filter 22d. The organic film filter 22d is formed on the light-receiving surface side of the photodiode 21c.

In addition, although not shown, one-layer organic film filters 22 is formed on each of the light-receiving surface side of the photodiodes 21 included in the pixels F4 to F6, similar to the pixel F1 and F3. Additionally, the substrate 20, the pixels F1 to F6, and the circuit 13 are fixed using a clear mold 23. Additionally, an IR cutoff filter 24 that cuts off a near-infrared component of incident light, and an UVF 25 that cuts off an ultraviolet component of excitation light emitted by the light source 11 are formed on the clear mold 23 on the light-receiving surface side of the pixels F. Light of 780 nm or more does not enter the pixels F due to the IR cutoff filter 24.

Figure 4:
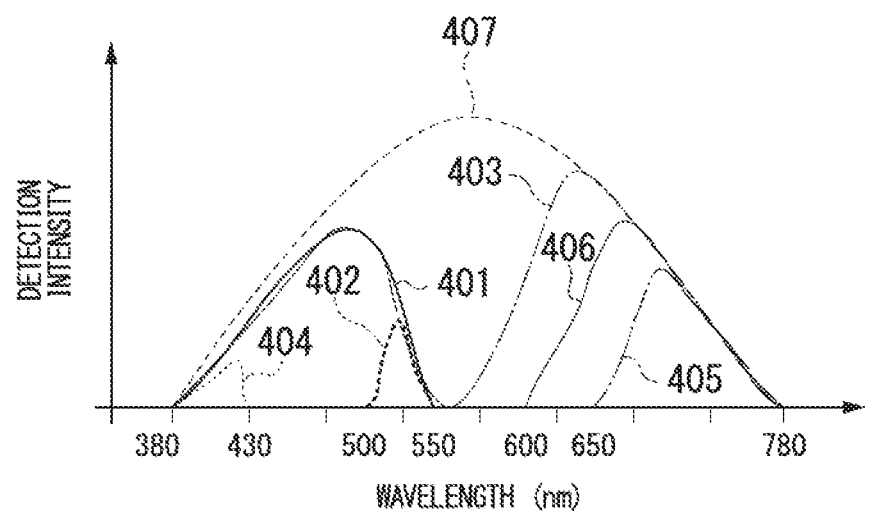
FIG. 4 is a graph showing the spectral sensitivity characteristics of the pixels of the present embodiment.

Next, the spectral sensitivity characteristics of the pixels F1 to F6 and a pixel F in which no organic film filter 22 is arranged will be described. FIG. 4 is a graph showing the spectral sensitivity characteristics of the pixels F1 to F6 of the present embodiment and the pixel F in which no organic film filter 22 is arranged. A horizontal axis of the graph shown in FIG. 4 represents wavelength (nm) and a vertical axis thereof represents output. Additionally, the graph shown in FIG. 4 illustrates a curve 401 representing the spectral sensitivity characteristics of the pixel F1, a curve 402 representing the spectral sensitivity characteristics of the pixel F2, a curve 403 representing the spectral sensitivity characteristics of the pixel F3, a curve 404 representing the spectral sensitivity characteristics of the pixel F4, a curve 405 representing the spectral sensitivity characteristics of the pixel F5, a curve 406 representing the spectral sensitivity characteristics of the pixel F6, and a curve 407 representing the spectral sensitivity characteristics of the pixel F in which no organic film filter 22 is arranged. In this as the wavelengths of light to be detected varies for each of pixels F1 to F6.

As shown in FIG. 4, the pixel F1 has spectral sensitivity characteristics (curve 401) in which a full width at half maximum is about 85 nm, and mainly light of 380 nm or more and 550 nm or less can be detected. Additionally, the pixel F2 has spectral sensitivity characteristics (curve 402) in which the full width at half maximum is about 50 nm, and mainly light of 500 nm or more and 550 nm or less can be detected. Additionally, the pixel F3 has spectral sensitivity characteristics (curve 403) in which the full width at half maximum is about 85 nm and mainly light of 180 nm or more and 550 nm or less can be detected, and in which the full width at half maximum is about 115 nm, and mainly light of 550 nm or more and 780 nm or less can be detected. Additionally, the pixel F4 has spectral sensitivity characteristics (curve 404) in which the full width at half maximum is about 45 nm, and mainly light of 380 nm or more and 430 nm or less can be detected. Additionally, the pixel F5 has spectral sensitivity characteristics (curve 405) in which the fill width at half maximum is about 65 nm. and mainly light of 650 nm or more and 780 nm or less can be detected. Additionally the pixel F6 has spectral sensitivity characteristics (curve 406) in which the full width at half maximum is about 90 nm, and mainly light of 600 nm or more and 780 nm or less can be detected. Additionally the spectral sensitivity characteristics (curve 407) of the pixel F in which no organic film filter 22 is arranged are spectral sensitivity characteristics which is realized by the overlapping between the spectral sensitivity characteristics of the photodiode 21 and a curve in which the transmittance of light of 780 nm or more by the IR cutoff filter 24 becomes zero, and in Which the full width at half maximum is about 200 nm, and mainly light of 380 nm or more and 780 nm or less can be detected.

In addition, the full width at half maximums of the organic film filters 22 formed on the light-receiving surface side of the photodiode of each of the pixels F1 to F6 have a characteristic having a larger width than a bandpass filter and the fluorescence of the banknote 14 in an example that is known in the related art. Additionally the organic film filter 22d formed on the light-receiving surface side of the photodiode 21c of the pixel F3 is a band elimination type. The organic film filter 22a, formed on the light-receiving surface side of the pixel F1 is a low-pass type. The organic film filters 22b and 22c funned on the pixel F2 corresponds to overlapping of a high-pass type filter and a low-pass type filter. Additionally, the organic film filter 22 formed on the light-receiving surface side of the photodiode of the pixel F4 is a bandpass type. The organic film filter 22 formed on the pixel F5 is a high-pass type.

Next, the configuration of the organic film filters 22 arranged on the light-receiving surface side of the photodiode of each of the pixels F1 to F6 will be described. In the present embodiment, the spectral sensitivity characteristics shown in FIG. 4 are realized by forming general-purpose organic film filters 22 through overlapping, when the spectral sensitivity characteristics shown in FIG. 4 cannot be realized by a single general-purpose organic film filter 22.

Figure 5:
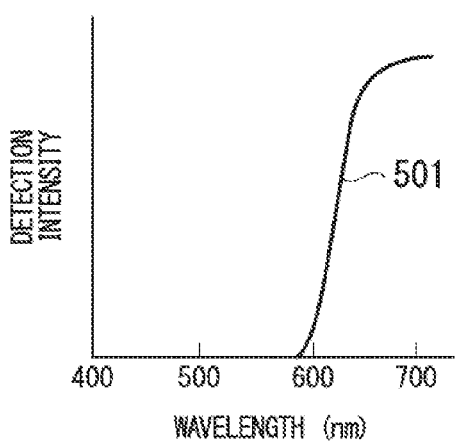
FIG. 5 is a graph showing the spectral sensitivity characteristics of a general-purpose organic film filter that transmits red light in the present embodiment.

FIG. 5 is a graph showing the spectral sensitivity characteristics of a general-purpose organic film filter 22 that transmits red light in the present embodiment. A vertical axis of the graph shown in FIG. 5 represents detection intensity, and a horizontal axis thereof represents wavelength (nm). A curve 501 represents the spectral sensitivity characteristics of the general-purpose organic film filter 22 that transmits red light. As shown, the general-purpose organic film filter 22 that transmits red light transmits light with a wavelength of 600 nm or more. In this way, the general-purpose organic film filter 22 that transmits red light is a high-pass type color filter.

Figure 6:
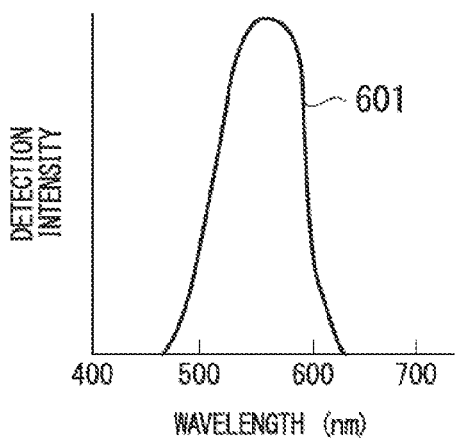
FIG. 6 is a graph showing the spectral sensitivity characteristics of a general-purpose organic film filter that transmits green light in the present embodiment.

FIG. 6 is a graph showing the spectral sensitivity characteristics of a general-purpose organic film filter 22 that transmits green light in the present embodiment. A vertical axis of the graph shown in FIG. 6 represents detection intensity, and a horizontal axis thereof represents wavelength (nm). A curse 601 represents the spectral sensitivity characteristics of the general-purpose organic film filler 22 that transmits green light. As shown in FIG. 6, the general-purpose organic film filter 22 that transmits green light transmits light with a wavelength from near 500 nm to near 600 nm. In this way, the general-purpose organic film filter 22 that transmits green light is a bandpass type color filter.

Figure 7:
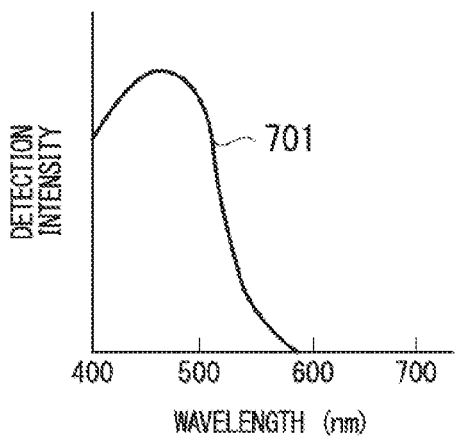
FIG. 7 is a graph showing the spectral sensitivity characteristics of a general-purpose organic film filter that transmits blue light in the present embodiment.

FIG. 7 is a graph showing the spectral sensitivity characteristics of a general-purpose organic film filter 22 that transmits blue light in the present embodiment. A vertical axis of the graph shown in FIG. 7 represents detection intensity, and a horizontal axis thereof represents wavelength (nm). A curve 701 represents the spectral sensitivity characteristics of the general-purpose organic film filter 22 that transmits blue light. As shown in FIG. 7 the general-purpose organic film filter 22 that transmits blue light transmits light with a wavelength of near 550 nm or less. In this way, the general-purpose organic film filter 22 that transmits blue light is a low-pass type color filter.

Figure 8:
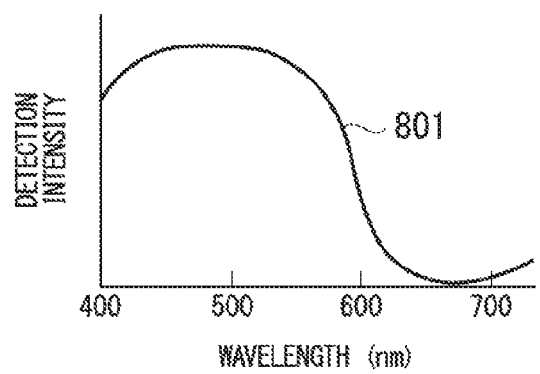
FIG. 8 is a graph showing the spectral sensitivity characteristics of a general-purpose organic film filter that transmits cyan light in the present embodiment.

FIG. 8 is a graph showing the spectral sensitivity characteristics of a general-purpose organic film filter 22 that transmits an light in the present embodiment A vertical axis of the graph shown in FIG. 8 represents detection intensity, and a horizontal axis thereof represents wavelength (nm). A curve 801 represents the spectral sensitivity characteristics of the general-purpose organic film filter 22 that transmits cyan light. As shown in FIG. 8, the general-purpose organic film filter 22 that transmits cyan light transmits light with a wavelength of near 600 nm or less. In this way, the general-purpose organic film filter 22 that transmits cyan light is a low-pass type color filter.

Figure 9:
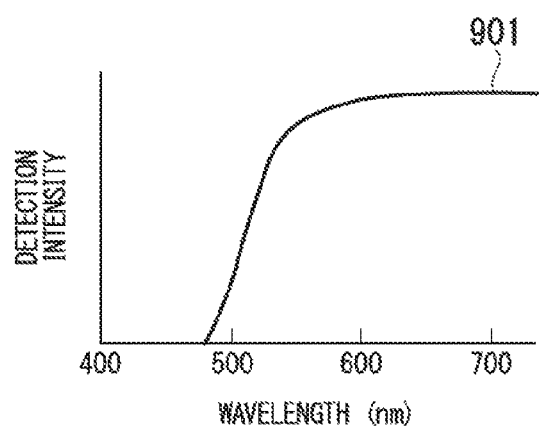
FIG. 9 is a graph showing the spectral sensitivity characteristics of a general-purpose organic film filter that transmits yellow light in the present embodiment.

FIG. 9 is a graph showing the spectral sensitivity characteristics of a general-purpose organic film filter 22 that transmits yellow light in the present embodiment. A vertical axis of the graph shown in FIG. 9 represents detection intensity, and a horizontal axis thereof represents wavelength (nm). A curve 901 represents the spectral sensitivity characteristics of the general-purpose organic film filter 22 that transmits yellow light. As shown in FIG. 9, the general-purpose organic film filter 22 that, transmits yellow light transmits light with a wavelength of near 500 nm or more. In this way the general-purpose organic film filter 22 that transmits yellow light is a high-pass type color filter.

Figure 10:
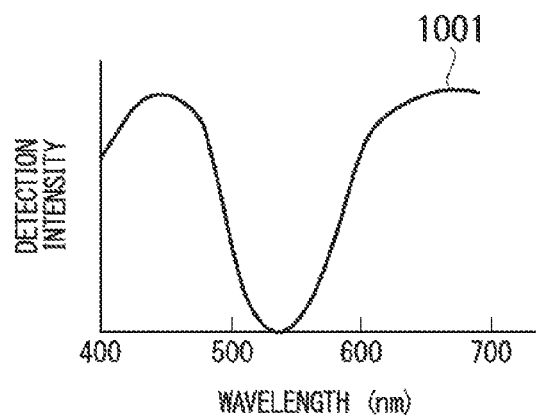
FIG. 10 is a graph showing the spectral sensitivity characteristics of a general-purpose organic film filter that transmits magenta light in the present embodiment.

FIG. 10 is a graph showing the spectral sensitivity characteristics of a general-purpose organic film filter 22 that transmits magenta light in the present embodiment. A vertical axis of the graph shown in FIG. 10 represents detection intensity, and a horizontal axis thereof represents wavelength (nm). A curve 1001 represents the spectral sensitivity characteristics of the general-purpose organic film filter 22 that transmits magenta light. As shown in FIG. 10, the general-purpose organic film filter 22 that transmits magenta light transmits light with a wavelength of 400 nm or more and near 500 nm and light with a wavelength of near 550 nm or more. In this way the general-purpose organic film filter 22 that transmits magenta light is a band elimination type color filter.

Figure 11:
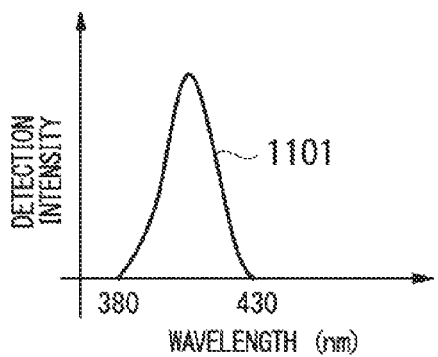
FIG. 11 is a graph showing the spectral sensitivity characteristics of a general-purpose organic film filter that transmits violet light in the present embodiment.

FIG. 11 is a graph showing the spectral sensitivity characteristics of a general-purpose organic film filter 22 that transmits violet light in the present embodiment. A vertical axis of the graph shown in FIG. 11 represents detection intensity, and a horizontal axis thereof represents wavelength (nm). A curve 1101 represents the spectral sensitivity characteristics of the general-purpose organic film filter 22 that transmits violet light. As shown in FIG. 11, the general-purpose organic film filter 22 that transmits violet light transmits light with a wavelength from near 380 nm to near 430 nm. In this way, the general-purpose organic film filter 22 that transmits violet light is a bandpass type color filter.

Figure 12A:
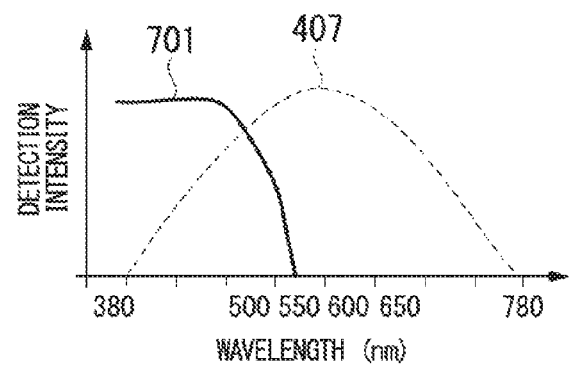
FIG. 12A is a graph of the transmission wavelengths of the general-purpose organic film filter that transmits blue light and the spectral sensitivity characteristics of a photodiode in a case where only an IR cutoff filter is present and there is no organic film filter.
Figure 12B:
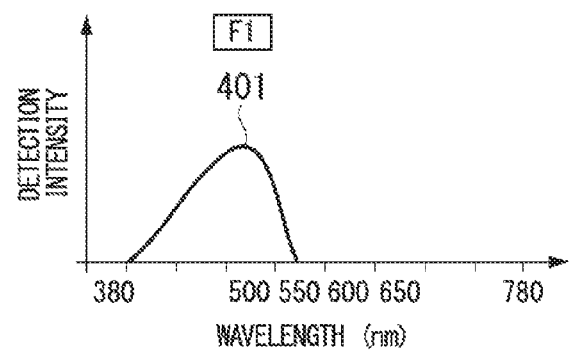
FIG. 12B is a graph of the spectral sensitivity characteristics of the pixels when the transmission wavelengths of the organic film filter and the spectral sensitivity characteristics of the photodiode that are shown in FIG. 12A overlap each other.

Next, the general-purpose organic, film filter 22a used in order to obtain the spectral sensitivity characteristics of the pixel F1 will be described. FIGS. 12A and 12B are graphs showing the spectral sensitivity characteristics of the general-purpose organic film filter 22a used in order to obtain the spectral sensitivity characteristics of the pixel F1 in the present embodiment. Vertical axes of the graphs shown in FIGS. 12A and 12B represent detection intensity, and horizontal axes thereof represent wavelength (nm). As shown in FIG. 12A when the transmission wavelength (curve 701) of the general-purpose organic film filter 22a that transmits blue light, and the spectral sensitivity characteristics (curie 407) of the photodiode 21 in a case where only the IR cutoff filter 24 is present and there is no organic film filter 22a overlap each other, as shown in FIG. 12B, the spectral sensitivity characteristics (curve 401) of the pixel F1 can be obtained.

The spectral sensitivity characteristics (curve 407) of the photodiode 21 in the case where only the IR cutoff filter 24 is present and there is no organic film filter 22, starts at 380 nm due to the spectral sensitivity characteristics of the photodiode 21, and since light of 780 nm or more is cut off by the IR cutoff filter 24, ends at 780 nm. Additionally, the general-purpose organic film filter 22 that transmits blue light is an organic low-pass type color filter, and the transmission wavelengths are as being shown in the curve 701. Due to this overlapping, the spectral sensitivity characteristics (curve 401) of the pixel F1 becomes spectral sensitivity characteristics in which the fill width at half maximum is about 85 nm and mainly light of 380 nm or more and 550 nm or less can be detected.

Therefore, the pixel F1 can be formed by forming the general-purpose organic film filter 22a, which transmits blue light, on the light-receiving surface side of the photodiode 21. That is, the pixel F1 includes the general-purpose organic film filter 22a that transmits blue light.

Figure 13A:
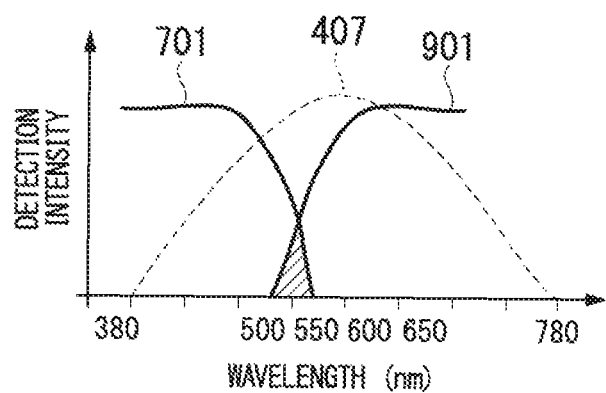
FIG. 13A is a graph of the transmission wavelengths of the general-purpose organic film filter that transmits blue light, the transmission wavelengths of the general-purpose organic film filter that transmits yellow light, and the spectral sensitivity characteristics of the photodiode in a case where only the IR cutoff filter is present and there is no organic film filter.
Figure 13B:
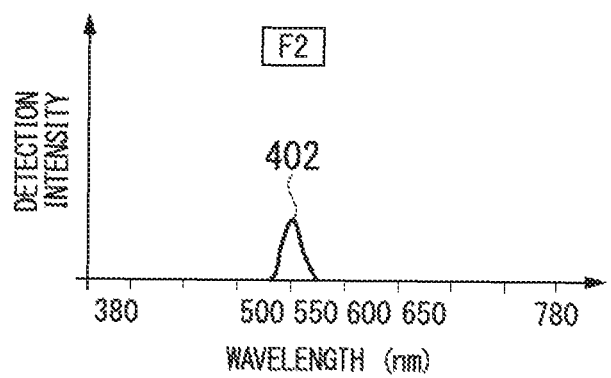
FIG. 13B is a graph of the spectral sensitivity characteristics of the pixels when the transmission wavelengths of the two organic film filters and the spectral sensitivity characteristics of the photodiode that are shown in FIG. 13A overlap each other.

Next, the general-purpose organic film filter 22b and 22c used in order to obtain the spectral sensitivity characteristics of the pixel F2 will be described. FIGS. 13A and 13B are graphs shoving the spectral sensitivity characteristics of the general-purpose organic film filter 22b and 22c used in order to obtain the spectral sensitivity characteristics of the pixel F2 in the present embodiment. Vertical axes of the graphs shown, in FIGS. 13A and 13B represent detection intensity and horizontal axes thereof represent wavelength (nm). As shown in FIG. 13A, when the transmission wavelength (curve 701) of the general-purpose organic film filter 22b that transmits blue light, the transmission wavelength (curve 901) of the general-purpose organic film filter 22c that transmits yellow light, and the spectral sensitivity characteristics (curve 407) of the photodiode 21 in the case where only the IR cutoff filter 24 is present and there is no organic film filter 22 overlap each other, as shown in FIG. 13B, the spectral sensitivity characteristics (curve 402) of the pixel F2 can be obtained.

The spectral sensitivity characteristics (curve 407) of the photodiode 21 in the case where only the IR cutoff filter 24 is present and there is no organic film filter 22 starts at 380 nm due to the spectral sensitivity characteristics of the photodiode 21, and since light of 780 nm or more is cut off by the IR cutoff filter 24, ends at 780 nm. Additionally the general-purpose organic film filter 22b that transmits blue light is an organic low-pass type color filter, and the transmission wavelength is as being shown in the curve 701. Additionally, the general-purpose organic film filter 22c that transmits yellow light is an organic high-pass type color filter, and the transmission wavelength is as being shown in the curve 901. Due to this overlapping, the spectral sensitivity characteristics (curve 402) of the pixel F2 become spectral sensitivity characteristics in which the full width at half maximum is about 50 nm and mainly light of 500 nm or more and 550 nm or less can be detected.

Therefore, the pixel F2 can be formed by stacking the general-purpose organic film filter 22b which transmits blue light and the general-purpose organic film filter 22c which transmits yellow light on the light-receiving surface side of the photodiode 21. That is, the pixel F2 includes the general-purpose organic film filter 22b that transmits blue light, and the general-purpose organic film filter 22c that transmits yellow light.

Figure 14A:
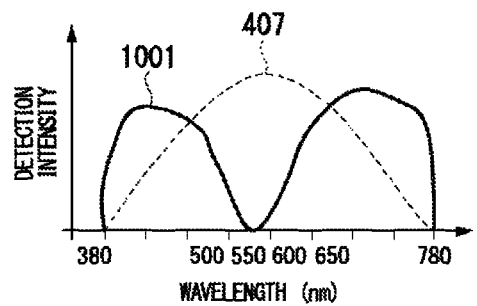
FIG. 14A is a graph of the transmission wavelengths of the general-purpose organic film filter that transmits magenta light, and the spectral sensitivity characteristics of the photodiode in the case where only the IR cutoff filter is present and there is no organic film filter.
Figure 14B:
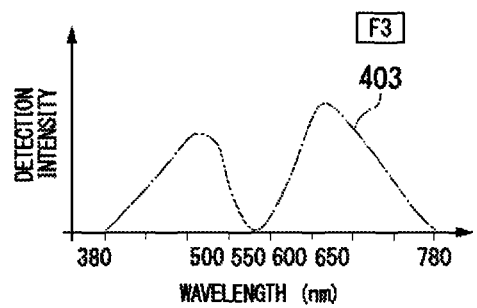
FIG. 14B is a graph of the spectral sensitivity characteristics of the pixels when the transmission wavelengths of the organic film filter and the spectral sensitivity characteristics of the photodiode that are shown in FIG. 14A overlap each other.

Next, the general-purpose organic film filter 22d used in order to obtain the spectral sensitivity characteristics of the pixel F3 will be described. FIGS. 14A and 14B are graphs showing the spectral sensitivity characteristics of the general-purpose organic film filter 22d used in order to obtain the spectral sensitivity characteristics of the pixel F3 in the present embodiment. Vertical axes of the graphs shown in FIGS. 14A and 14B represent detection intensity and horizontal axes thereof represent wavelength (nm). As shown in FIG. 14A, when the transmission wavelength (curve 1001) of the general-purpose organic film filter 22d that transmits magenta light, and the spectral sensitivity characteristics (curve 407) of the photodiode 21 in the case where only the IP, cutoff filter 24 is present and there is no organic film filter 22d overlap each other, as shown in FIG. 14B. the spectral sensitivity characteristics (curve 403) of the pixel F3 can be obtained.

The spectral sensitivity characteristics (curve 407) of the photodiode 21 in the case where only the IR cutoff filter 24 is present and there is no organic film filter 22 starts at 380 nm due to the spectral sensitivity characteristics of the photodiode 21, and since light of 780 nm or more is cut off by the IR cutoff filter 24, ends at 780 nm. Additionally, the general-purpose organic film filter 22 that transmits magenta light is an organic band elimination type color filter, and the transmission wavelength is as being shown in the curve 1001. Due to this overlapping, the spectral sensitivity characteristics (curve 403) of the pixel F3 are spectral sensitivity characteristics in which the full width at half maximum is about 85 nm, and mainly light of 380 nm or more and 550 nm or less can be detected and in which the full width at half maximum is about 115 nm and mainly light a 550 nm or more and 780 nm or less can be detected.

Therefore, the pixel F3 can be formed by forming the general-purpose organic film filter 22, which transmits magenta light, on the light-receiving surface side of the photodiode 21. That is, the pixel F3 includes the general-purpose organic film filter 22 that transmits magenta light.

Figure 15A:
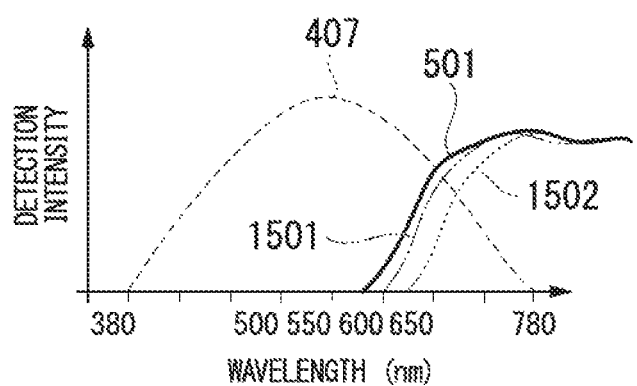
FIG. 15A is a graph of the transmission wavelengths of the organic film filter, and the spectral sensitivity characteristics of a photodiode in a case where there is no filter.
Figure 15B:
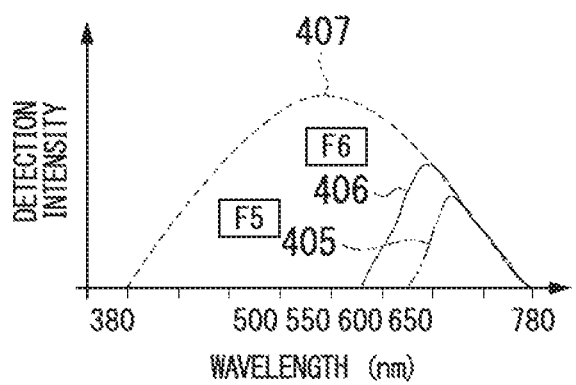
FIG. 15B is a graph of the spectral sensitivity characteristics of the pixels when the transmission wavelengths of the organic film filter and the spectral sensitivity characteristics of the photodiode that are shown in FIG. 15A overlap each other.

Next, the general-purpose organic film filters 22 used in order to obtain the spectral sensitivity characteristics of the pixels F5 and F6 will be described. FIGS. 15A and 15B are graphs shoving the spectral sensitivity characteristics of the general-purpose organic film filters 22 used in order to obtain the spectral sensitivity characteristics of the pixels F5 and F6 in the present embodiment. Vertical axes of the graphs shown in FIGS. 15A and 15B represent detection intensity and horizontal axes thereof represent wavelength (nm). In the present embodiment, the general-purpose organic film filters 22 that have different thicknesses and transmit two kinds of red light are used. Even in the same organic film filters 22, when thickness is increased, spectral sensitivity characteristics are slightly shifted to a long wavelength side. Due to this characteristic, even in the organic film filters 22 that transmit light of the same color, two kinds of spectral sensitivity characteristics can be realized by changing thickness.

FIG. 5 illustrates the general-purpose organic film filter 22 (curve 501) shown in FIG. 15A that transmits red light, the general-purpose organic film filter 22 (curve 1501) that is thicker than this filter and transmits red light, the general-purpose organic film filter 22 (curve 1502), which is 25 nm thicker than the general-purpose organic film filter 22 (curve 501) shown in FIG. 5 that transmits red light and which transmits red light, and the spectral sensitivity characteristics (curve 407) of the photodiode 21 in the case where there is no filter.

The general-purpose organic film filter 22 that transmits red light is an organic high-pass type color filter, and the transmission wavelength is as being shown in the curve 501. By arranging the general-purpose organic film filter 22, which transmits red light, in the photodiode 21, the spectral sensitivity characteristics (curve 406) of the pixel F6 become spectral sensitivity characteristics in which the full width at half maximum is about 90 nm, and mainly light of 600 nm or more and 780 nm or less can be detected.

Additionally, the transmission wavelength of the general-purpose organic film filter 22, which is 25 nm thicker than the general-purpose organic film filter 22 (curve. 501) shown in FIG. 5 that transmits red light and which transmits red light, is as shown in a curve 1502. By increasing the thickness of the organic film filter 22 by 25 nm in this way a transmission band can be shifted to the long wavelength side by 25 nm. By arranging, in the photodiode 21, the general-purpose organic film filter 22, which is 25 nm thicker than the general-purpose organic film filter 22 (curve 501) shown in FIG. 5 that transmits red light, and that transmits red light, the spectral sensitivity characteristics of the pixel F5 (curve 405) become spectral sensitivity characteristics in which the full width at half maximum is about 55 nm, and mainly light of 650 nm or more and 780 nm. or less can be detected.

The spectral sensitivity characteristics (curve 407) of the photodiode 21 in the case where only the IR cutoff filter 24 is present and there is no organic film filter 22 starts at 380 nm due to the spectral sensitivity characteristics of the photodiode 21, and since light of 780 nm or more is cut off by the IR cutoff filter 24, ends at 780 nm. Additionally, the general-purpose organic film filter 22 that transmits red light is an organic high-pass type color filter, and the transmission wavelength is as being shown in the curve 501. Due to this overlapping, the spectral sensitivity characteristics (curve 406) of the pixel F6 become spectral sensitivity characteristics in which the full width at half maximum is about 90 nm and mainly light of 600 nm or more and 780 nm or less can be detected.

Therefore, the pixel F6 can be formed by forming the general-purpose organic film filter 22 (curve 501) shown in FIG. 5, which transmits red light, on the light-receiving surface side of the photodiode 21. That is, the pixel F6 includes the general-purpose organic film filter 22 (curve 501) shown in FIG. 5 that transmits red light.

The general-purpose organic film filter 22, which that is 25 nm thicker than the general-purpose organic film filter 22 (curve 501) shown in FIG. 5 that transmits red light and which transmits red light, is an organic high-pass type color filter, and the transmission wavelength is as being shown in a curve 1502. Due to this overlapping, the spectral sensitivity characteristics (curve 405) of the pixel F5 become spectral sensitivity characteristics in which the full width at half maximum is about 65 nm and mainly light of 650 nm or more and 780 nm or less can be detected.

Additionally, the pixel F5 can be formed by forming the transmission wavelengths of the general-purpose organic film filter 22, which is 25 nm thicker than the general-purpose organic film filter 22 (curve 501) shown in FIG. 5 that transmits red light and which transmits red light, on the light-receiving surface side of the photodiode 21. That is, the pixel F5 include the general-purpose organic film filter 22, which is 25 nm thicker than the general-purpose organic film filter 22 (curve 501) shown in FIG. 5 that transmits red light and which transmits red light.

Figure 16A:
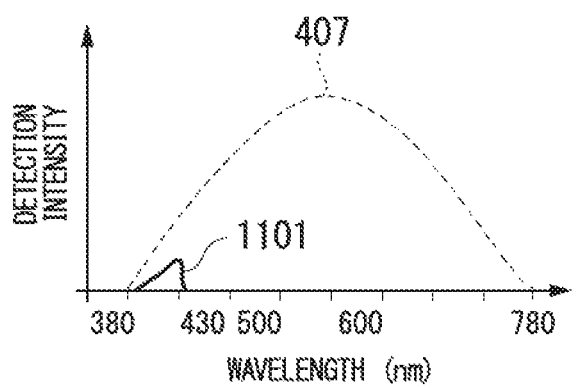
FIG. 16A is a graph of the transmission wavelengths of the general-purpose organic film filter that transmits violet light, and the spectral sensitivity characteristics of the photodiode in the case where only the IR cutoff filter is present and there is organic film filter.
Figure 16B:
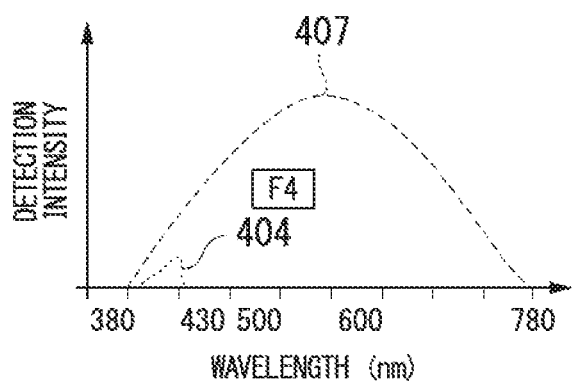
FIG. 16B is a graph of the spectral sensitivity characteristics of the pixels when the transmission wavelengths of the organic film filter and the spectral sensitivity characteristics of the photodiode that are shown in FIG. 16A overlap each other.

Next, the general-purpose organic, film filter 22 used in order to obtain the spectral sensitivity characteristics of the pixel F4 will be described. FIGS. 16A and 16B are graphs showing, the spectral sensitivity characteristics of the general-purpose organic film filter 22 used in order to obtain the spectral sensitivity characteristics of the pixel F4 in the present embodiment. Vertical axes of the shown graphs represent detection intensity, and horizontal axes thereof represent wavelength (nm). As shown in FIG. 16A, when the transmission wavelength (curve 1101) of the general-purpose organic film filter 22 that transmits violet light, and the spectral sensitivity characteristics (curve 407) of the photodiode 21 in the case where only the IR cutoff filter 24 is present and there is no organic film filter 22 overlap each other, as shown in FIG. 16B, the spectral sensitivity characteristics (curve 404) of the pixel F4 can be obtained.

The spectral sensitivity characteristics (curve 407) of the photodiode 21 in the case where only the IR cutoff filter 24 is present and there is no organic film filter 22 starts at 380 nm due to the spectral sensitivity characteristics of the photodiode 21, and since light of 780 nm or more is cut off by the IR cutoff filter 24, ends at 780 nm. Additionally, the general-purpose organic film filter 22 that transmits violet light is an organic bandpass type color filter, and the transmission wavelength is as being shown in the curve 1101, According to this overlapping, the spectral sensitivity characteristics (curve 404) of the pixel F4 become spectral sensitivity characteristics in which the full width at half maximum is about 45 nm and mainly light of 380 nm or more and 430 nm or less can be detected.

Therefore, the pixel F4 can be formed by forming the general-purpose organic film filter 22, which transmits violet light, on the light-receiving surface side of the photodiode 21. That is, the pixel F4 includes the general-purpose organic film filter 22 that transmits violet light.

Figure 17A:
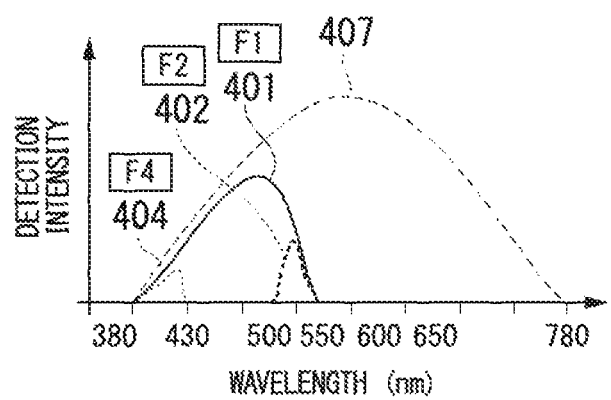
FIG. 17A is a graph of the transmission wavelengths of the organic film filler, and the spectral sensitivity characteristics of the photodiode in a case where there is no filter.
Figure 17B:
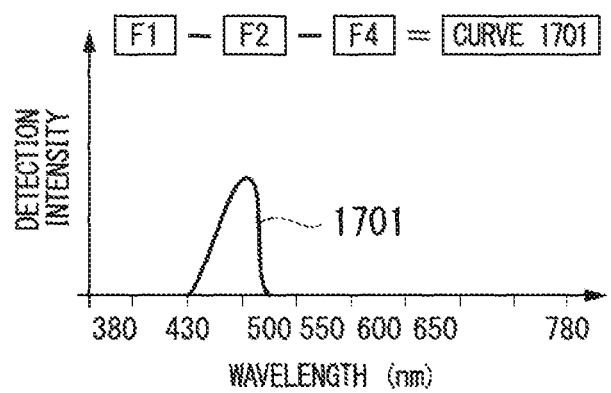
FIG. 17B is a graph of the spectral sensitivity characteristics of the pixels when the transmission wavelengths of the organic film filter and the spectral sensitivity characteristics of the photodiode that are shown in FIG. 17A overlap each other.

Next, a method of obtaining spectral sensitivity characteristics with a narrower bandwidth than the spectral sensitivity characteristics of the pixel F1 shown in FIG. 4 will be described. FIGS. 17A and 17B are graphs showing a method of obtaining spectral sensitivity characteristics with a narrower bandwidth than the spectral sensitivity characteristics of the pixel F1, using the spectral sensitivity characteristics of the pixel F the spectral sensitivity characteristics of the pixel F2, and the spectral sensitivity characteristics of the pixel F4 in the present embodiment. Vertical axes of the shown graphs represent detection intensity, and horizontal axes thereof represent wavelength (nm). FIG. 17A illustrates the spectral sensitivity characteristics (curve 401) of the pixel F1, the spectral sensitivity characteristics (curve 402) of the pixel F2, the spectral sensitivity characteristics (curve 404) of the pixel F4, and the spectral sensitivity characteristics (curve 407) of the pixel F in which the organic film filter 22 is not arranged. By the spectral processor 16 subtracting the spectral sensitivity characteristics of the pixel F2 and the spectral sensitivity characteristics of the pixel F4 from the spectral sensitivity characteristics of the pixel F1, as shown in FIG. 17B, the spectral sensitivity characteristics (curve 1701) with a band narrower than the spectral sensitivity characteristics of the pixel F1 can be obtained.

In this way, narrow band characteristics can be obtained by removing the components of the spectral sensitivity characteristics of unnecessary bands of the pixel F1 of the organic film filter 22, using the output of other pixels F2 and F4. Therefore, the spectral processor 16 can subtract pixel signals output by the pixels F2 and F4 via the pixel circuit from a pixel signal output by the pixel F1 via the pixel circuit, thereby calculating the intensity of light of the spectral sensitivity characteristics shown by the curve 1701 with a band narrower than the spectral sensitivity characteristics of the pixel F1. That is, the spectral processor 16 performs the four arithmetic operations on the plurality of pixel signals output by the plurality of pixel circuits corresponding to the pixel F1, F2 and F4, thereby calculating the light intensity of a light of spectral sensitivity characteristics with a band narrower than spectral sensitivity characteristics of a light that transmits through the organic film filter 22 of the pixel F1 (a light received by the pixel F1).

Figure 18A:
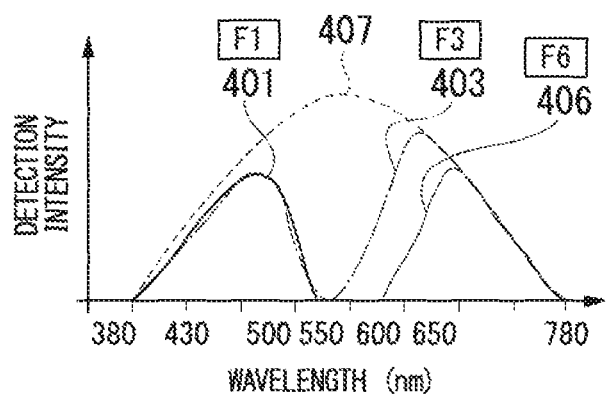
FIG. 18A is a graph of the spectral sensitivity characteristics of the pixels in which organic film filters are arranged, and the spectral sensitivity characteristics of the pixels in which no organic film filter is arranged.
Figure 18B:
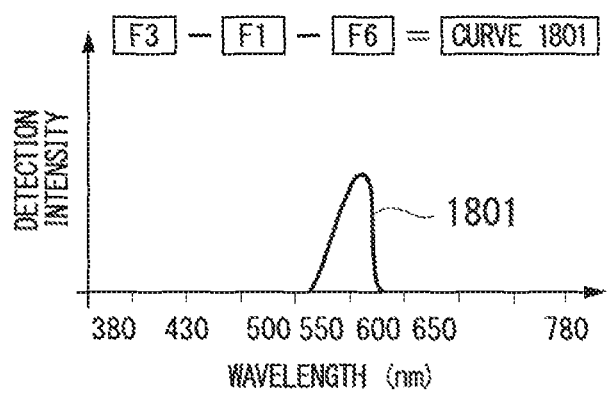
FIG. 18B is a graph in which the respective spectral sensitivity characteristics shown in FIG. 18A are subtracted.

Next, a method of obtaining spectral sensitivity characteristics narrower bandwidth than the spectral sensitivity characteristics of the pixel F3 shown in FIG. 4 will be described. FIGS. 18A and 18B are graphs showing a method of obtaining spectral sensitivity characteristics narrower than the spectral sensitivity characteristics of the pixel F3, using the spectral sensitivity characteristics of the pixel F3, the spectral sensitivity characteristics of the pixel F1, and the spectral sensitivity characteristics of the pixel F6 in the present embodiment. Vertical axes of the graphs shown in FIGS. 18A and 18B represent detection intensity, and horizontal axes thereof represent wavelength (nm). FIG. 18A illustrates the spectral sensitivity characteristics (curve 403) of the pixel F3, the spectral sensitivity characteristics (curve 401) of the pixel F1, the spectral sensitivity characteristics (curve 406) of the pixel F6, and the spectral sensitivity characteristics (curve 407) of the pixel F in which the organic film filter 22 is not arranged. By the spectral processor 16 subtracting the spectral sensitivity characteristics of the pixel F1 and the spectral sensitivity characteristics of the pixel F6 from the spectral sensitivity characteristics of the pixel F3, as shown in FIG. 18B, the spectral sensitivity characteristics (curve 1801) with a band narrower than the spectral sensitivity characteristics of the pixel F3 can be obtained.

In this way, narrow band characteristics can be obtained by removing the components of the spectral sensitivity characteristics of unnecessary bands of the pixel F3 left by the overlapping of the organic film filter 22, using the output of other pixels F1 and F6. Therefore, the spectral processor 16 can subtract pixel signals output by the pixels F1 and F6 via the pixel circuit from a pixel signal output by the pixel F3 via the pixel circuit, thereby calculating the intensity of light of the spectral sensitivity characteristics shown by the curve 1801 with a band narrower than the spectral sensitivity characteristics of the pixel F3. That is, the spectral processor 16 performs the four arithmetic operations on the plurality of pixel signals output by the plurality of pixel circuits corresponding to the pixel F1, F3 and F6, thereby calculating a light intensity of a light of spectral sensitivity characteristics with a band narrower than spectral sensitivity characteristics of a light that transmits through the organic film filter 22 of the pixel F3 (a light received by the pixel F3).

Figure 19A:
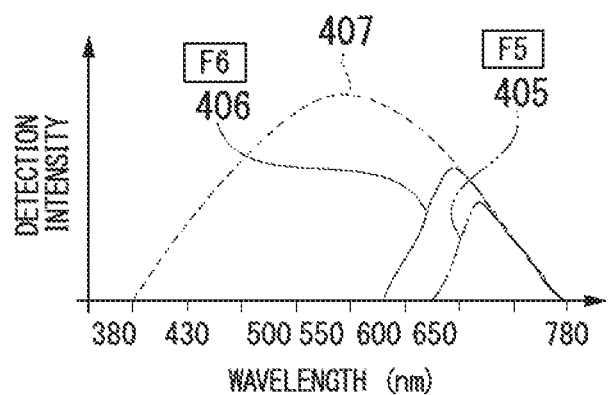
FIG. 19A is a graph of the spectral sensitivity characteristics of the pixels in which organic film filters are arranged, and the spectral sensitivity characteristics of the pixels in which no organic film filter is arranged.
Figure 19B:
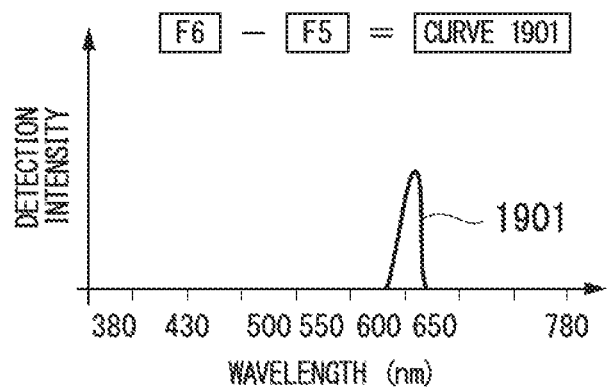
FIG. 19B is a graph in which the respective spectral sensitivity characteristics shown in FIG. 19A are subtracted.

Next, a method of obtaining spectral sensitivity characteristics narrower than the spectral sensitivity characteristics of the pixel F6 shown in FIG. 4 will be described. FIGS. 19A and 19B are graphs showing a method of obtaining spectral sensitivity characteristics narrower than the spectral sensitivity characteristics of the pixel F6, using the spectral sensitivity characteristics of the pixel 6 and the spectral sensitivity characteristics of the pixel F5 in the present embodiment. Vertical axes of the graphs shown in FIGS. 19A and 19B represent detection intensity, and horizontal axes thereof represent wavelength (nm). FIG. 19A illustrates the spectral sensitivity characteristics (curve 406) of the pixel F6, the spectral sensitivity characteristics (curve 405) of the pixel F5, and the spectral sensitivity characteristics (curve 407) of the pixel F in which the organic film filter 22 is not arranged. By the spectral processor 15 subtracting the spectral sensitivity characteristics of the pixel F5 from the spectral sensitivity characteristics of the pixel F6, as shown in FIG. 19B, the spectral sensitivity characteristics (curve 1901) with a hand narrower than the spectral sensitivity characteristics of the pixel F6 can be obtained.

In this way, narrow band characteristics can be obtained by removing the components of the spectral sensitivity characteristics of unnecessary bands of the pixel F6 left by the overlapping of the organic film filter 22, using the output of another pixel F5. Therefore, the spectral processor 16 can subtract a pixel signal output by the pixel F5 via the pixel circuit from a pixel signal output by the pixel F5 via the pixel circuit, thereby calculating the intensity of light of the spectral sensitivity characteristics shown by the curve 1901 with a band narrower than the spectral sensitivity characteristics of the pixel F6. That is, the spectral processor 16 performs the four arithmetic operations on the plurality of pixel signals output by the plurality of pixel circuits corresponding to the pixel F5 and F6, thereby calculating a light intensity of a light of spectral sensitivity characteristics with a band narrower than spectral sensitivity characteristics of a light that transmits through the organic film filter 22 of the pixel F6 (a light received us the pixel F6).

Figure 20A:
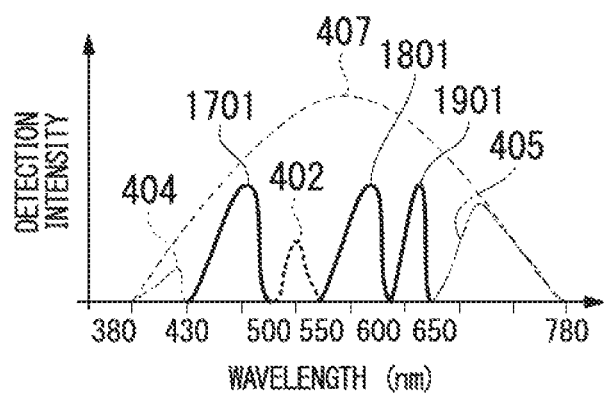
FIG. 20A is a graph of the spectral sensitivity characteristics of the pixels in which organic film filters are arranged, and the spectral sensitivity characteristics of the pixels in which no organic film filter is arranged.
Figure 20B:
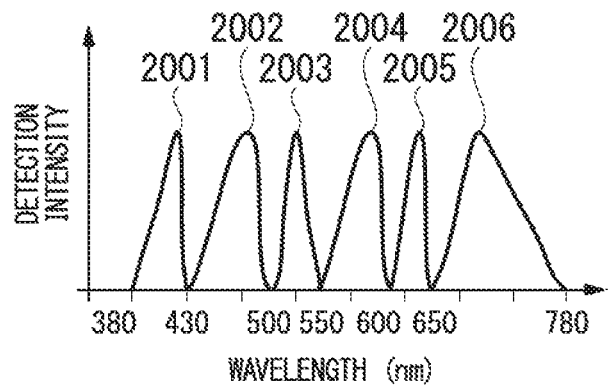
FIG. 20B is a graph in which the respective spectral sensitivity characteristics shown in FIG. 20A are subtracted.

Next, an example in which each of the pixel circuits in the circuit 13 amplifies pixel signals will be described. FIGS. 20A and 20B are graphs showing an example in which each of the pixel circuits in the circuit 13 amplifies pixel signals in the present embodiment. Vertical axes of the graphs shown in FIGS. 20A and 20B represent detection intensity, and horizontal axes thereof represent wavelength (nm). FIG. 20A illustrates the spectral sensitivity characteristics (curve 402) of the pixel F2, the spectral sensitivity characteristics (curve 404) of the pixel F4, the spectral sensitivity characteristics (curve 405) of the pixel F5, the spectral sensitivity characteristics (curves 1701, 1801, and 1901) calculated by the spectral processor 16, and the spectral sensitivity characteristics (curve 407) of the pixel F in which the organic film filter 22 is not arranged.

As shown in FIG. 20A, the detection intensities of the spectral sensitivity characteristics (curve 402) of the pixel F2, the spectral sensitivity characteristics (curve 404) of the pixel F4, the spectral sensitivity characteristics (curve 405) of the pixel F5, and the spectral sensitivity characteristics (curves 1701, 1801, and 1901) calculated by the spectral processor 16 are different from each other. Thus, in the present embodiment, the output gains of the pixels F1 to F6 are adjusted such that the respective detection intensities become the same. That is, the output gains of the pixel circuits corresponding to the pixels are adjusted according to the output of the spectral processor 16. FIG. 20B illustrates the spectral sensitivity characteristics when the output gains of the pixels F1 to F6 are adjusted so that the detection intensities of the spectral sensitivity characteristics (curve 402) of the pixel F2, the spectral sensitivity characteristics (curve 404) of the pixel F4, the spectral sensitivity characteristics (curve 405) of the pixel F5, and the spectral sensitivity characteristics (curves 1701, 1801, and 1901) calculated by the spectral processor 16, become the same.

The curve 1901 becomes a curve 2001 after a gain is adjusted. Additionally, the curve 1701 becomes a curve 2002 after a gain is adjusted. Additionally, the et 1801 becomes a curve 2003 after a gain is adjusted. Additionally, the curve 404 becomes a curve 2004 after a gain is adjusted. Additionally, the curve 405 becomes a curve 2005 after a gain is adjusted.

When each of the pixel circuits in the circuit 13 adjusts the output gains of the pixels F1 to F6, as shown in FIG. 20B, the detection intensities of the spectral sensitivity characteristics (curve 402) of the pixel F2, the spectral sensitivity characteristics (curve 404) of the pixel F4, the spectral sensitivity characteristics (curve 405) of the pixel F5, and the spectral sensitivity characteristics (curves 1701, 1801, and 1901) calculated by the spectral processor 16 become the same. That is, a light beam (curve 2001) with the wavelengths of a narrow band S1, a light beam (curve 2002) with the wavelengths of a narrow band S2, a light beam (curve 2003) with the wavelengths of a narrow hand S3, a light beam (curve 2004) with the wavelengths of a narrow band S4, a light beam (curve 2005) with the wavelengths of a narrow band S5, and a light beam (curve 2006) with the wavelengths of a narrow band S6 can be detected with the same intensity.

In addition, the organic multilayer filter fluorescent sensor 12 may include the pixel F in which no organic film filter 22 is formed, and the pixel may be used for the above processing. Additionally, for example, each of the pixel circuits in the circuit 13 may adjust the output gain of the pixel F in which the organic film filter 22 is formed by using the output of the pixel F in which no organic film filter 22 is formed as a reference output. Thus, even when the output of the pixel F in which the organic film filter 22 is formed is adjusted, the output of the pixel F in which no organic film filter 22 is formed can be used.

As shown in FIG. 20B, the banknote discrimination apparatus 1 can detect the intensities of the light beams with the wavelengths of the narrow bands S1 to S6. Accordingly, for example, discrimination between a green fluorescent substance printed on the banknote 14 and a green fluorescent pen, when such discrimination was difficult, can be easily performed.

Figure 21:
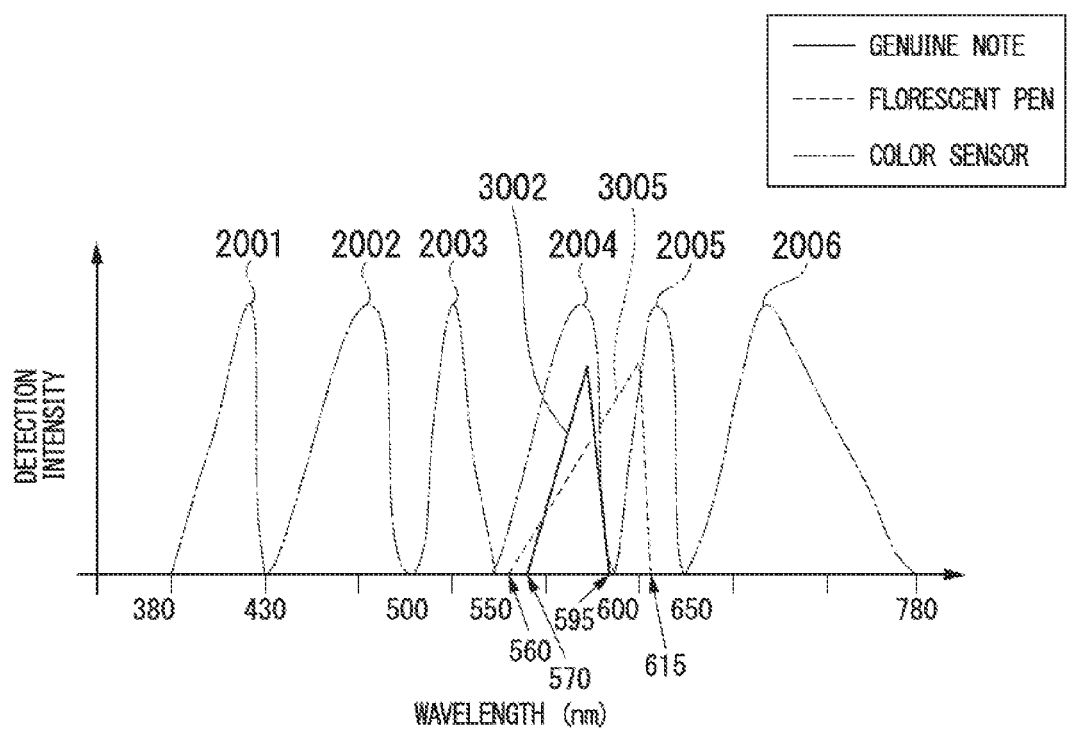
FIG. 21 is a graph showing the narrow bands of lights capable of being detected by the banknote discrimination apparatus, the band of light emitted as a green fluorescence band, and the hand of light emitted by a green fluorescent pen, in the present embodiment.

FIG. 21 is a graph showing the narrow bands S1 to S6 of the light beams capable of being detected by the banknote discrimination apparatus 1, the band of light emitted by a green fluorescence band, and the band of light emitted by the green fluorescent pen in the present embodiment. A vertical axis of the graph shown in FIG. 21 represents detection intensity, and a horizontal axis thereof represents wavelength (nm). A line 3002 represents the band of light emitted by the green fluorescence band printed on a genuine note. A line 3005 represents the band of light emitted by the green fluorescent pen. As shown in FIG. 21, the band (line 3002) of the light emitted by the green fluorescent substance printed on a new banknote, and the band (line 3005) of light emitted by the green fluorescent pen are close to each other.

The banknote discrimination apparatus 1 in the present embodiment can detect the intensity of light of the narrow band S4, thereby detecting the intensity of the light emitted by the green fluorescent substance printed on the genuine note. Additionally, it is possible to detect the intensity of light of the narrow band S5, thereby detecting the intensity of the light emitted by the green fluorescent pen without emission of light from the green fluorescent substance printed on the genuine note. That is, since the intensity of the light emitted by the green fluorescent substance printed on the genuine note, and the intensity of the light emitted by the green fluorescent pen can be individually detected, whether or not the banknote 14 is genuine can be more precisely determined. Specifically, the discriminator 17 determines that the banknote 14 is a genuine note when only the light of the narrow band S4 is detected on the basis of the processing result of the spectral processor 16 and determines that the banknote 14 is a forged banknote when the light of the narrow band S5 is also detected. In addition, the method for determining whether or not the banknote 14 is genuine is performed using the same method as a method known in the related art.

Additionally, in the present embodiment, only the general-purpose organic film filters 22 are used, and the intensities of the light beams with the respective wavelengths of the narrow bands S1 to S6 are detected by the overlapping of the general-purpose organic film filters 22 and the four arithmetic operations on the outputs of the plurality of pixels F. The general-purpose organic film filters 22 can be formed by being miniaturized to micron sizes utilizing a semiconductor manufacturing process for sensors, such as an image sensor and a scanner, and being coated on pixels, such as the photodiodes 21. Therefore, high accuracy can be realized along with reduction in size and costs.

Figure 22:
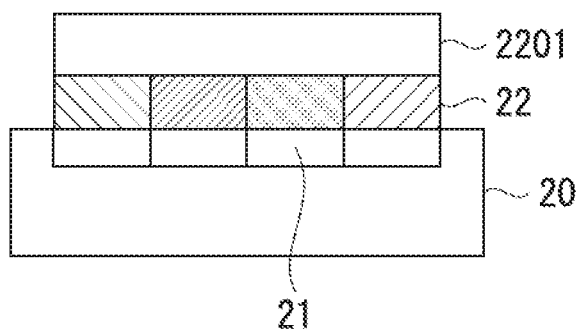
FIG. 22 is a sectional view showing another configuration of the organic multilayer filter fluorescent sensor in the present embodiment.

In addition, the configuration of the organic multilayer filter fluorescent sensor 12 is not limited to the example shown in FIG. 3. FIG. 22 is a sectional view showing another configuration of the organic multilayer filter fluorescent sensor 12 in the present embodiment. As shown in FIG. 22, the photodiodes 21 are formed on the substrate 20. Additionally, the plurality of organic film filters 22 are formed on a glass substrate 2201 that is separate from the substrate 20. Additionally, the plurality of organic film filters 22 formed on the glass substrate 2201 are arranged such that a surface on which the organic film filters 22 are formed and light-receiving surfaces of the photodiodes 21 face each other.

In this way, in order to detect the light emitted by the fluorescent substance and the fluorescent pen stably and independently of the incidence angle of the light transmitted through the organic film filters 22, arranging the organic film filters 22 are arranged on a lower surface (photodiode 21 side) of the glass substrate 2201 can be considered. That is, when the photodiodes 21 and the organic, film filters 22 are separately formed, it is possible to bring the surfaces of the organic, film filters 22 as close to the light-receiving surfaces of the photodiodes 21 as possible, thereby allowing stably detection of the color (spectrum) of the light that has entered obliquely.

Figure 23:
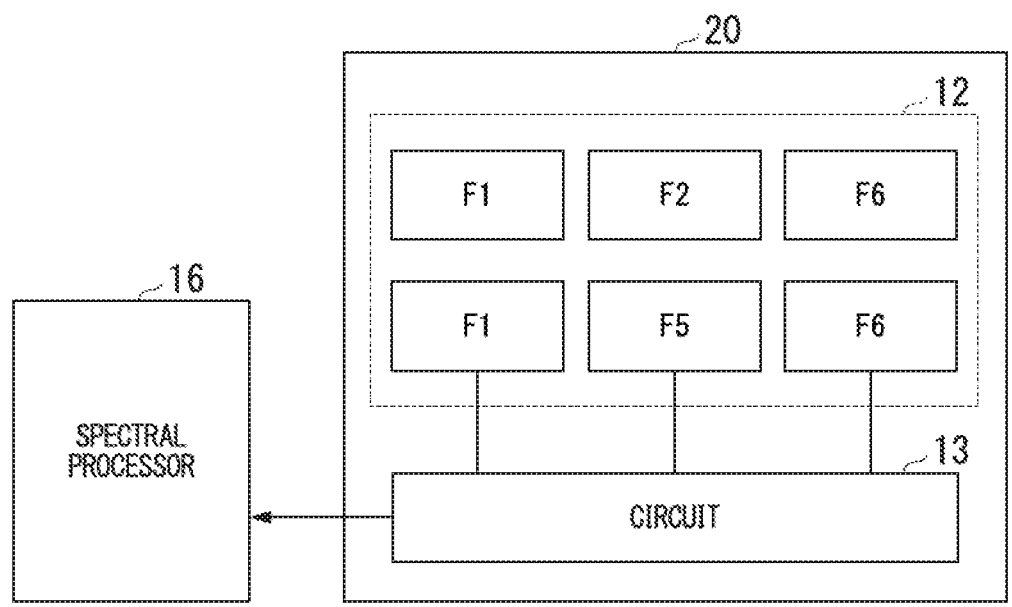
FIG. 23 is a schematic view showing still another configuration of the organic multilayer filter fluorescent sensor in the present embodiment.
Figure 24:
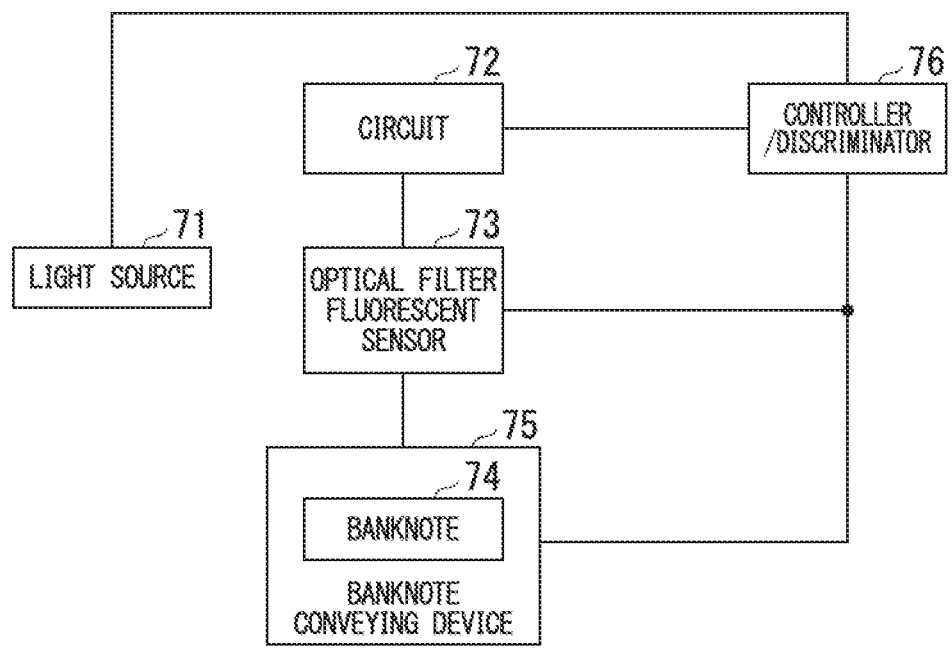
FIG. 24 is a configuration view of a banknote discrimination apparatus that is known in the related art.

Additionally, the arrangement of the pixels F included in the organic multilayer filter fluorescent sensor 12 is not limited to the example shown in FIG. 2. FIG. 23 is a schematic view showing still another configuration of the organic multilayer filter fluorescent sensor 12 in the present embodiment. As shown FIG. 23 the organic multilayer filter fluorescent sensor 12 includes a total of six pixels F of two pixels F1, a pixel F2, a pixel F5, and two pixels F6 on the substrate 20. In this way, the organic multilayer filter fluorescent sensor 12 may include a plurality of identical pixels F. Additionally the number of pixels F included in the organic multilayer filter fluorescent sensor 12 is not limited to six, and may be an arbitrary number. Since the outputs of the identical pixels F can be averaged by including the plurality of identical pixels F the precision of pixel signals output by the pixels F can be improved. Therefore, the banknote discrimination apparatus 1 can perform reliable discrimination between the banknotes 14.

Additionally although the organic multilayer filter fluorescent sensor 12 forms a pair of organic film filters 22 corresponding to the split photodiodes 21, the filter sensor is not limited to this. For example, a CMOS image sensor, a contact image sensor (CIS), or the like may be arranged instead of the split photodiodes 21 and the organic film filters 22 may be formed on these sensors or the like.

The banknote discrimination apparatus 1 may include a computer processor. Processes in the spectral processor 16 and the discriminator 17 may be executed by the computer processor.

While preferred embodiments of the present invention have been described and shown above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A banknote discrimination apparatus comprising:
   a plurality of photoelectric conversion elements in which an incident light including fluorescence emitted from a banknote irradiated with excitation light enters;
   a plurality of organic film filters that are arranged so as to overlap each of the plurality of photoelectric conversion elements, and have mutually different transmission bands;
   a circuit including a plurality of pixel circuits which are respectively connected to one corresponding element among the plurality of photoelectric conversion elements and output a pixel signal converted by each photoelectric conversion element in accordance with an intensity of the incident light that transmits through the organic film filter and enters to the photoelectric conversion element;
   a spectral processor which outputs incident light intensities of light that has narrower wavelength bands than a wavelength bands of lights that transmit through the organic film filters based on the plurality of pixel signals output by the plurality of pixel circuits; and
   a discriminator which compares an output pattern output from the spectral processor with a prerecorded signal pattern of a genuine note in order to discriminate between whether or not a banknote is genuine,
   wherein at least one of the plurality of organic film filters is a filter obtained by stacking two or more filter layers.

2. The banknote discrimination apparatus according to claim 1,
   wherein the transmission wavelength band of each of the plurality of organic film filters includes at least a partial band within 380 nm to 1100 nm, and
   wherein each of the plurality of organic film filters is any one type of a bandpass filter type, a high-pass filter type, a low-pass filter type, and a band elimination type.

3. The banknote discrimination apparatus according to claim 1,
   wherein colors of several filters among the plurality of organic film filters are the same, and thicknesses of the several filters are different from each other.

4. The banknote discrimination apparatus according to claim 1, wherein colors of several filters among the plurality of organic film filters are the same, and concentrations of coloring materials for the several filters are different from each other.

5. The banknote discrimination apparatus according to claim 1,
   wherein a pixel on which the organic film filter is not arranged is included.

6. The banknote discrimination apparatus according to claim 1,
   wherein the spectral processor performs the four arithmetic operations on the plurality of pixel signals output by the plurality of pixel circuits, thereby outputting the light intensity of a light of spectral sensitivity characteristics with a band narrower than spectral sensitivity characteristics of the light that transmits through the organic film filter.

7. The banknote discrimination apparatus according to claim 1,
   wherein each of the plurality of pixel circuits adjusts output gains of the pixel circuits according to an output of the spectral processor.

8. The banknote discrimination apparatus according to claim 1,
   wherein the transmission band of the wavelengths of a light detected by the photoelectric conversion element on which each organic film filter is arranged includes at least one of a partial transmission band of which the full width at half maximum is 45 nm or more and 350 nm or less and the wavelength band is 380 nm or more and 1100 nm or less, and a partial transmission band of which the full width at half maximum is 150 nm or more and 210 nm or less and the wavelength band is 550 nm or more and 1100 nm or less.

9. The banknote discrimination apparatus according to claim 1,
   wherein each of the plurality of organic, film filters is formed using any one of a filter that transmits red light, a filter that transmits green light, a filter that transmits blue light, a filter that transmits cyan light, a filter that transmits yellow light, a filter that transmits magenta light, and a filter that transmits violet light.

10. The banknote discrimination apparatus according to claim 1,
    wherein the photoelectric conversion element on which each organic film filter is arranged has a near-infrared light component cutoff filter on a light-receiving surface.

11. The banknote discrimination apparatus according to claim 1,
    wherein the plurality of organic film filters are formed on a glass substrate separately from the photoelectric conversion elements.

12. The banknote discrimination apparatus according to claim 11,
    wherein the plurality of organic film filters are arranged on the glass substrate so that a surface of the glass substrate on which the plurality of organic film filters is formed faces light-receiving surfaces of the plurality of photoelectric conversion elements.

13. The banknote discrimination apparatus according to claim 1,
    wherein the plurality of organic film filters include filters that transmit light of a same color.

* * * * *